United States Patent [19]

Beck et al.

[11] Patent Number: 4,563,210

[45] Date of Patent: Jan. 7, 1986

[54] HERBICIDAL 5-HALO-1-HALOPHENYL-1H-PYRAZOLE-4-CARBONITRILES

[75] Inventors: James R. Beck, Indianapolis; Michael P. Lynch, Greenfield, both of Ind.

[73] Assignee: Eli Lilly and Company, Indianapolis, Ind.

[21] Appl. No.: 650,135

[22] Filed: Sep. 13, 1984

Related U.S. Application Data

[63] Continuation-in-part of Ser. No. 549,138, Nov. 7, 1983, abandoned.

[51] Int. Cl.[4] .................. A01N 43/56; C07D 231/14; C07D 231/16
[52] U.S. Cl. ........................... 71/92; 548/377; 548/378
[58] Field of Search .............. 548/377, 378; 71/92

[56] References Cited

U.S. PATENT DOCUMENTS

| | | | |
|---|---|---|---|
| 2,925,418 | 2/1960 | Druey et al. | 260/249.5 |
| 2,965,643 | 12/1960 | Druey et al. | 260/256.4 |
| 3,187,006 | 6/1965 | Druey et al. | 260/310 |
| 3,732,225 | 5/1973 | Breuer et al. | 260/256.4 |
| 3,760,084 | 9/1973 | Marsico et al. | 424/273 |
| 4,459,150 | 7/1984 | Hatton et al. | 71/92 |

FOREIGN PATENT DOCUMENTS

| | | | |
|---|---|---|---|
| 26034 | 4/1981 | European Pat. Off. | 548/362 |
| 1058519 | 6/1959 | Fed. Rep. of Germany | 548/362 |
| 29598 | 9/1965 | Japan | 548/362 |
| 70966 | 11/1972 | Japan | 548/362 |
| 884851 | 12/1961 | United Kingdom | 548/362 |
| 2070604 | 9/1981 | United Kingdom | 548/362 |

OTHER PUBLICATIONS

Derwent Abst. 73536v, (1974).
Southwick et al., "Prep. of 4,6-Diaminopyrazolo[3,4-d] Pyrimidines . . . ", J. Het. Chem., 1975, pp. 1199–1205.
Cheng et al., "Potential Purine Antagonists", J. Org. Chem., 23, pp. 852–861, (1958).
Cheng et al., "Potential Purine Antagonists", J. Org. Chem., 21, pp. 1240–1256, (1956).
Kinugawa et al., "Studies on Fungicides", Chem. Pharm. Bull., 12, (2), pp. 182–191, (1964).
Chem. Abst. 55, 13459f, (1961).
Chem. Abst. 94, 103295v, (1981).
Chem. Abst. 99, 70618a, (1983).
Khan et al., Pyrazole Derivatives I. Synthesis of Some Cyanopyrazoles. Rev. Latinoamer, Quim. 13, 100–102, (1982).
M. A. Khan & A. C. C. Freitas, "Fused Pyrazolopyrimidines. I. Pyrazolo[4,3-e]-v-triazolo[1,5-a] pyrimidine. A New Heterocyclic System. Nov., 1980, pp. 1603–1604, vol. 17.

Primary Examiner—Richard A. Schwartz
Assistant Examiner—Kurt G. Briscoe
Attorney, Agent, or Firm—Kathleen R. S. Page; Arthur R. Whale

[57] ABSTRACT

The present invention is directed to herbicidal compounds of the formula

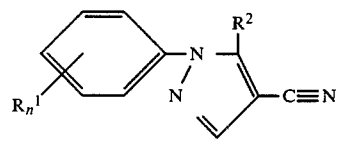

wherein each $R^1$ independently is halogen; $R_2$ is halo or trifluoromethyl; and n is 1–5; with the provisos that when n is 1, $R^1$ is other than fluorine, and when n is 2 and each $R^1$ is chlorine, at least one $R^1$ is located at a para or ortho position on the phenyl ring.

27 Claims, No Drawings

HERBICIDAL 5-HALO-1-HALOPHENYL-1H-PYRAZOLE-4-CARBONITRILES

CROSS-REFERENCE TO RELATED APPLICATIONS

This is a continuation-in-part of our application Ser. No. 549,138, filed Nov. 7, 1983, now abandoned.

SUMMARY OF THE INVENTION

The present invention relates to a compound of the formula

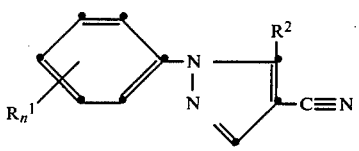

wherein each of $R^1$ independently is halogen; $R^2$ is halo or trifluoromethyl; and n is 1-5;

with the provisos that when n is 1, $R^1$ is other than fluorine, and when n is 2 and each $R^1$ is chlorine, at least one $R^1$ is located at a para or ortho position on the phenyl ring.

Compositions containing these compounds are disclosed, as well as a herbicidal method for their use.

DETAILED DESCRIPTION OF THE INVENTION

The term "halogen" as defined herein represents fluorine, chlorine, bromine and iodine. The preferred halogen atoms are chlorine and bromine.

The compounds of the present invention are readily prepared by the following detailed procedures. The preferred synthetic procedure for the $R^2$=halogen compounds involves reacting a phenylhydrazine analog with an (alkoxymethylene)malononitrile derivative to provide the corresponding 5-amino-1-phenyl-1H-pyrazole-4-carbonitrile derivative which is converted to the 5-halogen derivative by the reaction of a diazotizing agent in the presence of an appropriate halogenating agent. The reaction scheme for this process is as follows:

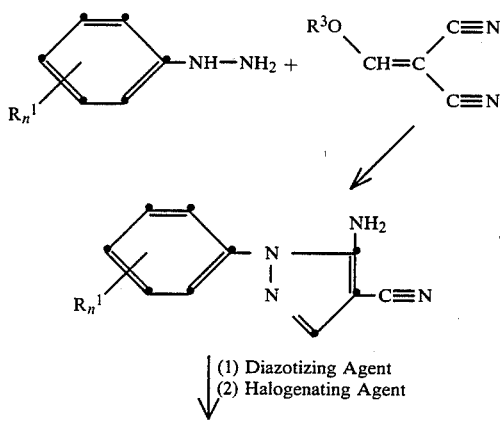

(1) Diazotizing Agent
(2) Halogenating Agent

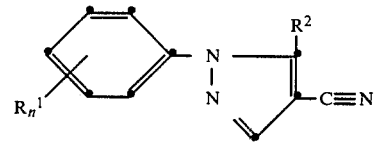

wherein $R^1$ and n are as defined above, $R^2$ is halogen, and $R^3$ is $C_1$-$C_6$ alkyl.

The first step of the synthetic procedure described above involves reacting approximately equimolar quantities of the reactants in the presence of acetic acid and water. Sodium acetate may also be present in the mixture. The reaction typically occurs at a temperature in the range of from about 50° C. to 200° C., more preferably from about 75° C. to the reflux temperature of the reaction mixture. The reaction is usually complete within twenty-four hours. The product is then typically isolated by filtration or may be extracted with a water immiscible organic solvent and concentrating the solution under reduced pressure. The carbonitrile thus formed can be further purified if needed by any of several routine methods, including crystallization from common solvents, chromatography over solid supports such as silica or alumina, and related purification techniques.

The process of converting the amino substituent at the 5-position of the pyrazole ring to halogen differs depending on the halogen atom desired. Compounds wherein $R^2$ on the pyrazole ring is chlorine are prepared by employing nitrosyl chloride as the diazotizing as well as the halogenating reagent. This reaction is conducted in a suitable solvent at a temperature in the range of from about 0° C. to 100° C., more preferably from about 10° C. to 30° C. Suitable solvents should be non-reactive and include most halogenated hydrocarbons such as chloroform, carbon tetrachloride, and the like. Typically, from one equivalent to a large excess of the nitrosyl chloride is simply bubbled into the reaction mixture. It is also preferred to have an acid catalyst present in the reaction mixture such as hydrochloric acid, hydrobromic acid and the like. The product is then usually isolated by evaporating the mixture to dryness under reduced pressure. The resulting residue may then be further purified if desired by any of several well known procedures such as crystallization or column chromatography.

Compounds of the present invention wherein $R^2$ on the pyrazole ring is bromine or iodine are prepared by employing an alkyl nitrite diazotizing agent and the corresponding halogen source as desired. Typical halogen sources include bromine, iodine, bromoform, iodoform and the like. Suitable alkyl nitrite diazotizing agents include but are not limited to t-butyl nitrite, isoamyl nitrite and the like. Typically the reaction is performed in a suitable organic solvent, such as chloroform or carbon tetrachloride, by addition of the alkyl nitrite dropwise into the reaction mixture. The reaction is usually complete after about 1 to 48 hours at a temperature between 0° C. to 100° C., more preferably at about 10° C. to 50° C. Typically the reaction is worked up by simply evaporating the reaction mixture to dryness under reduced pressure and purifying the residue, if desired, by standard techniques such as crystallization or column chromatography.

Compounds of the invention wherein $R^2$ is fluorine are preferably prepared by displacing chlorine from the corresponding pyrazolecarbonitrile. This reaction is conducted by adding the appropriate starting material dissolved in a suitable solvent to an excess of the fluorinating agent. Suitable solvents include DMF and DMSO, with the latter being preferred. Typical fluorinating agents include the alkali metal fluorinating agents such as potassium fluoride, sodium fluoride, and cesium fluoride. Before being used in the reaction, the fluorinating agent should be dried so as to remove any residual water. Generally this can be performed by refluxing the fluorinating agent with the aid of a Dean Stark trap in a water immiscible solvent such as toluene. The solvent is then removed before combining the reaction ingredients. The reaction is substantially complete after about 1 to 48 hours when conducted at a temperature in the range from about 75° to about 200° C., more preferably from about 100° C. to about 150° C. The product is then generally isolated by pouring the cooled reaction mixture into ice water and collecting the precipitated solid by filtration. The product thus isolated may then be purified if desired by routine procedures.

The phenylhydrazine and (alkoxymethylene)malononitrile starting materials are either commercially available or readily prepared by known procedures. For example, the preferred nitrile for use in the preferred reaction process described above, (ethoxymethylene)malononitrile, is commercially available. The phenylhydrazine derivatives may be prepared by reacting an aniline with sodium nitrite and stannous chloride in acid to provide the hydrazine salt, which can be converted to the free hydrazine with any suitable base.

The $R^2$=trifluoromethyl compounds of the present invention are prepared by the following reaction scheme:

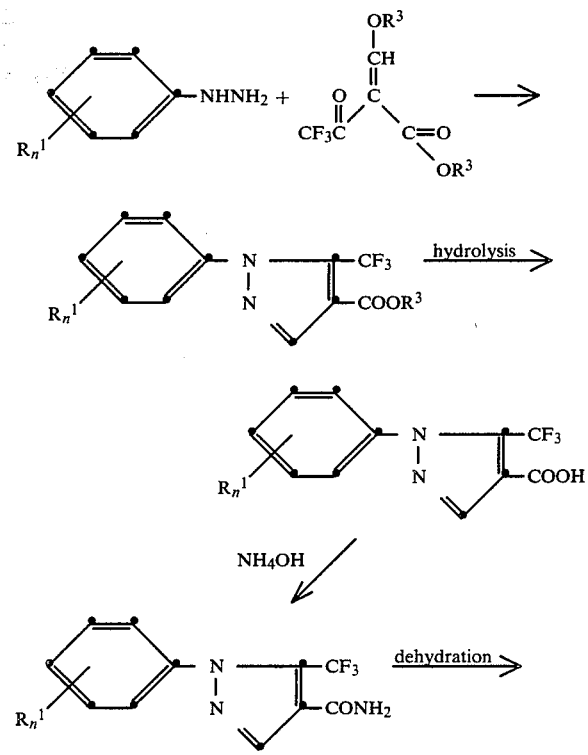

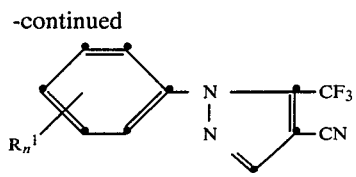

wherein $R^3 = C_1-C_6$ alkyl.

The reaction of phenylhydrazine with an alkyl(alkoxymethylene)trifluoroacetoacetate is readily practiced by known procedures. Typically the reaction is carried out in a suitable solvent such as methanol or ethanol, and at temperatures of from −25° to 0° C. Preferably equimolar quantities of the reactants are employed. Triethylamine or another acid scavenger can be employed. The product can be worked up in conventional procedures.

The conversion of the pyrazole carboxylic acid ester to the corresponding carboxylic acid is accomplished by well known hydrolysis conditions. This reaction is typically performed with a suitable base in a mutual organic solvent such as aqueous methanol or ethanol. Suitable bases include the alkali metal hydroxides, preferably sodium hydroxide and potassium hydroxide. Typically the reaction mixture is refluxed for about 1 to 24 hours and then acidified. The resulting precipitate may then be either extracted into a water immiscible solvent or collected by filtration. Purification may be performed if desired by any one of many standard techniques.

The conversion of the resulting pyrazole carboxylic acid to the corresponding pyrazole carboxamide is also accomplished by any of numerous conventional methods. Conveniently the pyrazole carboxylic acid is reacted with ammonium hydroxide in the presence of a coupling reagent to achieve the corresponding carboxamide. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as N-ethoxycarbonyl-2-ethoxy-1,2-dihydroquinoline (EEDQ). The direct coupling of the pyrazole carboxylic acid and ammonium hydroxide is carried out by adding about an equimolar quantity of the ammonium hydroxide to a solution of the carboxylic acid in the presence of an equimolar quantity or slight excess of coupling reagent. The reaction generally is carried out in an unreactive organic solvent such as dichloromethane or dimethylformamide, and usually is complete within about twenty-four hours when conducted at a temperature of about 0° to about 30° C. The product is then typically isolated by filtration. The carboxamide product thus formed can be further purified if needed by any of several routine methods, including crystallization from common solvents, chromatography over solid supports such as silica or alumina, and related purification techniques.

Finally, the pyrazole carboxamide is dehydrated to the desired pyrazole carbonitrile. This dehydration can be carried out with a number of reagents. In one suitable procedure, the pyrazole carboxamide is dehydrated by treatment with thionyl chloride and DMF; the reaction is conveniently carried out in a solvent such as toluene, and at temperatures of from 25° to 100° C. Workup is carried out in conventional techniques.

The alkyl(alkoxymethylene)trifluoroacetoacetates employed as starting materials in the foregoing reaction scheme are prepared by the method of R. Jones in *J. Am. Chem. Soc.*, 73, 3684 (1951).

The following Examples are illustrative of compounds of the present invention. These Examples are not intended to be limiting to the scope in any respect and should not be so construed.

EXAMPLE 1

5-Chloro-1-(2,3,4-trichlorophenyl)-1H-pyrazole-4-carbonitrile

A. 2,3,4-Trichlorophenylhydrazine

Fifty grams of 2,3,4-trichloroaniline was added portionwise to a solution of 200 ml of concentrated hydrochloric acid at approximately 0° C. To the reaction mixture was added 17.6 g of sodium nitrite dissolved in 100 ml of water dropwise over 1 hour. Next, 94.8 g of stannous chloride dissolved in 100 ml of concentrated hydrochloric acid was added dropwise to the reaction mixture over a 1 hour period while maintaining the temperature at approximately 0° C. The reaction mixture was stirred for approximately 1 hour at this temperature and then warmed to room temperature and stirred for 20 additional hours. The precipitated solid was collected by filtration and dried. The collected solid was added to a cold solution of 300 ml of 25% aqueous sodium hydroxide and this solution was stirred at approximately 5° C. for 1 hour. This aqueous solution was then extracted with ether and the organic phase was washed with water and saturated sodium chloride, and finally dried over anhydrous magnesium sulfate. The organic phase was evaporated under reduced pressure and the residue was recrystallized from ethanol to afford 35 g of 2,3,4-trichlorophenylhydrazine. Yield 66%. mp=138°–140° C.

Analysis was calculated for $C_6H_6Cl_3N_2$ Theory: C, 34.08; H, 2.38; N, 13.25; Found: C, 34.18; H, 2.44; N, 13.29.

B. 5-Amino-1-(2,3,4-trichlorophenyl)-1H-pyrazole-4-carbonitrile

A solution of 15 g of 2,3,4-trichlorophenylhydrazine, 8.7 g of (ethoxymethylene)malononitrile, 100 ml of glacial acetic acid and 50 ml of water was refluxed for 3 hours. The reaction mixture was cooled, poured into ice water and the precipitated solid was collected by filtration and dried. This solid was dissolved in ethyl acetate and the resulting solution was washed twice with saturated sodium bicarbonate, once with 100 ml of water, once with 100 ml of saturated brine and dried over anhydrous magnesium sulfate. The organic phase was evaporated under reduced pressure and the residue was recrystallized from ethanol to give 13.2 g of 5-amino-1-(2,3,4-trichlorophenyl)-1H-pyrazole-4-carbonitrile. Yield 66%. mp=140°–142° C.

Analysis calculated for $C_{10}H_5Cl_3N_4$ Theory: C, 41.77; H, 1.75; N, 19.49; Found: C, 41.43; H, 1.74; N, 19.50.

C. Nitrosyl chloride was bubbled into a solution of 3.4 g of 5-amino-1-(2,3,4-trichlorophenyl)-1H-pyrazole-4-carbonitrile dissolved in 150 ml of chloroform for approximately 5 minutes. The reaction mixture was cooled and the volatiles were removed in vacuo. The resulting residue was recrystallized from ethanol to provide 1.6 g of 5-chloro-1-(2,3,4-trichlorophenyl)-1H-pyrazole-4-carbonitrile. mp=124°–126° C.

Analysis calculated for $C_{10}H_3Cl_4N_3$ Theory: C, 39.13; H, 0.99; N, 13.69; Found: C, 39.35; H, 1.19; N, 13.92.

EXAMPLE 2

5-Chloro-1-(2,4-difluorophenyl)-1H-pyrazole-4-carbonitrile

Nitrosyl chloride was bubbled into a solution of 3.6 g of 5-amino-1-(2,4-difluorophenyl)-1H-pyrazole-4-carbonitrile in 150 ml of chloroform for 5 minutes. The solution was placed on the steam bath for 5 minutes, cooled and the solvent was removed under reduced pressure. The residue was recrystallized from ethanol to afford 3.2 g of 5-chloro-1-(2,4-difluorophenyl)-1H-pyrazole-4-carbonitrile. Yield 83%. mp=120°–122° C.

Analysis calculated for $C_{10}H_4ClF_2N_3$ Theory: C, 50.13; H, 1.68; N, 17.54; Found: C, 50.25; H, 1.71; N, 17.78.

EXAMPLE 3

5-Chloro-1-(2,4,6-trichlorophenyl)-1H-pyrazole-4-carbonitrile

Hydrochloric acid gas was bubbled into a solution of 5 g of 5-amino-1-(2,4,6-trichlorophenyl)-1H-pyrazole-4-carbonitrile in 100 ml of chloroform for approximately one minute. Nitrosyl chloride was then bubbled into the solution for several additional minutes and the reaction mixture was refluxed for approximately 20 minutes. The volatiles were removed under reduced pressure and the residue was recrystallized from ethanol to afford 2.1 g of 5-chloro-1-(2,4,6-trichlorophenyl)-1H-pyrazole-4-carbonitrile. mp=78°–79° C.

Analysis calculated for $C_{10}H_3Cl_4N_3$ Theory: C, 39.13; H, 0.99; N, 13.69; Found: C, 39.10; H, 1.10; N, 13.92.

EXAMPLE 4

5-Bromo-1-(2,4-dichlorophenyl)-1H-pyrazole-4-carbonitrile

To a solution of 5-amino-1-(2,4-dichlorophenyl)-1H-pyrazole-4-carbonitrile and 3 ml of bromine in 50 ml of chloroform was added 1.7 g of isoamyl nitrite. The reaction mixture was stirred at room temperature for approximately 10 minutes and then refluxed for approximately one hour. The solution was evaporated to dryness under reduced pressure and the residue was chromatographed over silica gel employing toluene as the eluent. Fractions containing the major component were combined and the solvent was evaporated therefrom to afford 0.8 g of 5-bromo-1-(2,4-dichlorophenyl)-1H-pyrazole-4-carbonitrile after crystallization from 3A alcohol. mp=101°–102° C.

Analysis calculated for $C_{10}H_4BrCl_2N_3$ Theory: C, 37.89; H, 1.27; N, 13.26; Found: C, 37.84; H, 1.39; N, 13.08.

The following Examples further illustrate compounds of the present invention and were prepared by the general procedures outlined above.

EXAMPLE 5

5-Chloro-1-(2,4-dibromophenyl)-1H-pyrazole-4-carbonitrile mp=102°–104° C.

Analysis calculated for $C_{10}H_4Br_2ClN_3$ Theory: C, 33.23; H, 1.12; N, 11.63; Found: C, 33.49; H, 1.35; N, 11.59.

EXAMPLE 6

5-Chloro-1-(2,3-dichlorophenyl)-1H-pyrazole-4-carbonitrile mp=121°–123° C.

Analysis calculated for $C_{10}H_4Cl_3N_3$ Theory: C, 44.07; H, 1.48; N, 15.42; Found: C, 44.07; H, 1.58; N, 15.52.

EXAMPLE 7

5-Chloro-1-(2,4,5-trichlorophenyl)-1H-pyrazole-4-carbonitrile mp=152°–154° C.

Analysis calculated for $C_{10}H_3Cl_4N_3$ Theory: C, 39.13; H, 0.99; N, 13.69; Found: C, 39.32; H, 1.28; N, 13.93.

EXAMPLE 8

5-Chloro-1-(2,3,4,5-tetrachlorophenyl)-1H-pyrazole-4-carbonitrile mp=161°–164° C.

Analysis calculated for $C_{10}H_2Cl_5N_3$ Theory: C, 35.18; H, 0.59; N, 12.31; Found: C, 35.40; H, 0.86; N, 12.36.

EXAMPLE 9

5-Chloro-1-(4-chlorophenyl)-1H-pyrazole-4-carbonitrile mp=134°–136° C.

Analysis calculated for $C_{10}H_5Cl_2N_3$ Theory: C, 50.45; H, 2.12; N, 17.65; Found: C, 50.43; H, 2.35; N, 17.61.

EXAMPLE 10

5-Chloro-1-(3-chlorophenyl)-1H-pyrazole-4-carbonitrile mp=108°–109° C.

Analysis calculated for $C_{10}H_5Cl_2N_3$ Theory: C, 50.45; H, 2.12; N, 17.65; Found: C, 50.72; H, 2.07; N, 17.85.

EXAMPLE 11

5-Chloro-1-(2-chlorophenyl)-1H-pyrazole-4-carbonitrile mp=101° C.

Analysis calculated for $C_{10}H_5Cl_2N_3$ Theory: C, 50.45; H, 2.12; N, 17.65; Found: C, 50.47; H, 1.98; N, 17.66.

EXAMPLE 12

5-Chloro-1-(2,4-dichlorophenyl)-1H-pyrazole-4-carbonitrile mp=90°–91° C.

Analysis calculated for $C_{10}H_4Cl_3N_3$ Theory: C, 44.07; H, 1.48; N, 15.42; Cl, 39.03; Found: C, 43.97; H, 1.64; N, 15.65; Cl, 38.75.

EXAMPLE 13

5-Chloro-1-(2,3,5,6-tetrafluorophenyl)-1H-pyrazole-4-carbonitrile mp=108°–110° C.

Analysis calculated for $C_{10}H_2ClF_4N_3$ Theory: C, 43.58; H, 0.73; N, 15.25; Found: C, 43.72; H, 1.01; N, 15.03.

EXAMPLE 14

5-Chloro-1-(4-bromophenyl)-1H-pyrazole-4-carbonitrile mp=140°–142° C.

Analysis calculated for $C_{10}H_5BrClN_3$ Theory: C, 42.51; H, 1.78; N, 14.87; Found: C, 42.48; H, 1.72; N, 15.05.

EXAMPLE 15

5-(Trifluoromethyl)-1-(2,4-dichlorophenyl)-1H-pyrazole-4-carbonitrile

A.

5-(Trifluoromethyl)-1-(2,4-dichlorophenyl)-1H-pyrazole-4-carboxylic acid, ethyl ester 2,4-Dichlorophenylhydrazine hydrochloride salt (15.68 grams, 0.068 mole) was dissolved in a minimum amount of ethanol and the solution was cooled to −10° C. Triethylamine (9.44 ml, 0.068 mole) was added followed by ethyl(ethoxymethylene)trifluoroacetoacetate (16.27 grams, 0.068 mole). The addition of this last reactant was made over thirty minutes, keeping the reaction temperature below −10° C. The reaction mixture was allowed to rise to room temperature overnight (about 16 hours). The solvent was removed in vacuo and the residue was dissolved in equal parts of ethyl acetate and water. The organic phase was separated, washed with 1N HCl, water, saturated sodium bicarbonate solution, water, and brine. It was then dried and evaporated to 7.85 grams of an oil which slowly crystallized. The 5-(trifluoromethyl)-1-(2,4-dichlorophenyl)-1H-pyrazole-4-carboxylic acid, ethyl ester, was recrystallized from petroleum ether, mp=81°–83° C.

B.

5-(Trifluoromethyl)-1-(2,4-dichlorophenyl)-1H-pyrazole-4-carboxylic acid 5-(Trifluoromethyl)-1-(2,4-dichlorophenyl)-1H-pyrazole-4-carboxylic acid, ethyl ester (3.31 grams, 0.0094 mole) and potassium hydroxide (0.8 gram, 0.014 mole) were combined in 25 ml of ethanol. The reaction mixture was refluxed for 2 hours, then poured into 150 ml of ice/water and filtered to remove solids. The remaining solution was acidified with concentrated HCl, filtered to separate the precipitate which was then dried and recrystallized from cyclohexane/toluene with charcoal, yielding 1.90 grams of 5-(trifluoromethyl)-1-(2,4-dichlorophenyl)-1H-pyrazole-4-carboxylic acid, mp=154°–155° C.

Analysis calculated for $C_{11}H_5Cl_2F_3N_2O_2$ Theory: C, 40.64; H, 1.55; N, 8.62; Found: C, 40.85; H, 1.79; N, 8.41.

C.

5-(Trifluoromethyl)-1-(2,4-dichlorophenyl)-1H-pyrazole-4-carboxamide 5-(Trifluoromethyl)-1-(2,4-dichlorophenyl)-1H-pyrazole-4-carboxylic acid (5.0 grams, 0.015 mole) and carbonyldiimidazole (2.74 grams, 0.017 mole) were dissolved in 35 ml of DMF. The solution was stirred for 10 minutes and ammonium hydroxide (8 ml) was then added. The reaction mixture was stirred at room temperature for 72 hours, then poured into 150 ml of ice/water. The product precipitated and was separated by filtration, dried, and recrystallized from toluene with charcoal, yielding 3.0 grams of 5-(trifluoromethyl)-1-(2,4-dichlorophenyl)-1H-pyrazole-4-carboxamide, mp=191°–193° C.

Analysis calculated for $C_{11}H_6Cl_2F_3N_3O$ Theory: C, 40.77; H, 1.87; N, 12.97; Found: C, 40.98; H, 2.02; N, 12.67.

D.
5-(Trifluoromethyl)-1-(2,4-dichlorophenyl)-1H-pyrazole-4-carbonitrile 5-(Trifluoromethyl)-1-(2,4-dichlorophenyl)-1H-pyrazole-4-carboxamide (2.36 grams, 0.073 mole) was suspended in 30 ml of toluene, 10 ml of thionyl chloride, and about 1 ml of DMF. The suspension was stirred and heated to reflux, then refluxed for 1½ hours. Solvent and excess thionyl chloride was removed in vacuo. The crude solid was crystallized from toluene yielding 5-(trifluoromethyl)-1-(2,4-dichlorophenyl)-1H-pyrazole-4-carbonitrile, yield 0.7 gram, mp=83°–85° C.

Analysis calculated for $C_{11}H_4Cl_2F_3N_3O$ Theory: C, 43.17; H, 1.32; N, 13.73; Found: C, 43.19; H, 1.58; N, 13.57.

EXAMPLE 16
5-(Trifluoromethyl)-1-(4-chlorophenyl)-1H-pyrazole-4-carbonitrile mp=95°–96° C.

Analysis calculated for $C_{11}H_5ClF_3N_3$ Theory: C, 48.64; H, 1.86; N, 15.47; Found: C, 48.45; H, 1.64; N, 15.51.

The compounds of the present invention are useful both as preemergent and postemergent herbicides. Therefore yet another embodiment of the invention is a method for controlling undesired plants which comprises applying to the plants or to the locus of the plants a growth inhibiting amount of a present compound.

The term "growth inhibiting amount", as defined herein, refers to an amount of a compound of the present invention which either kills or stunts the growth of the weed species for which control is desired. This amount will generally be from about 0.05 to about 20.0 pounds or greater of a compound of the invention per acre (about 0.056 to about 22.4 kg/ha). The compounds are more preferably applied at rates of about 0.10 to about 8.0 pounds per acre (about 0.112 to about 8.96 kg/ha). The exact concentration of active ingredient required varies with the weed species to be controlled, type of formulation, soil type, climate conditions and the like.

The term "undesired plants", as defined herein, refers to both weeds and weed seeds which are present at the location to be treated with an active agent of the present invention. These compounds can be applied to the soil to selectively control undesired plants by soil contact when the weed seeds are germinating and emerging. They can also be used directly to kill emerged weeds by direct contact with the exposed portion of the weed.

The compounds of the present invention are preferably formulated with a suitable agriculturally-acceptable carrier for ease of application. These compositions will typically contain from about 0.1 to about 95.0 percent by weight of the active ingredient, depending on the composition desired. Examples of typical herbicidal compositions contemplated by the present invention include sprayable formulations, such as wettable powders, aqueous suspensions and emulsifiable concentrates; and solid compositions, such as dusts and granules.

The most convenient formulations are in the form of concentrated compositions to be applied by spraying as water dispersions or emulsions containing in the range from about 0.1 percent to about 10 percent of the active agent by weight. Water-dispersible or emulsifiable compositions may be either solids, usually known as wettable powders, or liquids, usually known as emulsifiable concentrates and aqueous suspensions.

A typical wettable powder comprises an intimate mixture of an active ingredient of the invention, an inert carrier, and surfactants. The concentration of the active agent is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed naphthalenesulfonates, and the alkyl sulfates.

A typical emulsifiable concentrate comprises from about 0.1 to about 6 pounds of a compound of the invention per gallon of liquid (about 0.0112 to about 0.672 kg/l), dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

An aqueous suspension, or flowable, is comprised of a finely ground suspension of the active ingredient dispersed in a water based system. This type of formulation is particularly useful for compounds with low water solubility. The concentration of active agent is usually from about 15 to 60 percent by weight. A typical aqueous suspension may comprise wetting and dispersing agents, antifreeze components, thickening or bulking agents as well as water and the active ingredient.

Dust compositions containing a compound of the present invention usually contain from about 0.1 to about 10 percent by weight of the compound. Dusts are prepared by intimately mixing and finely grinding the active agent with an inert solid such as ground montmorillonite clay, attapulgite clay, talc, ground volcanic rock, kaolin clay, or other inert, relatively dense, inexpensive substances.

Solid, granular compositions are convenient for the application of compounds of this invention to the soil and will contain the active agent in an amount from about 0.1 to about 20 percent by weight. Granules comprise a compound of the invention dispersed on a granular inert carrier such as coarsely ground clay of from about 0.1 to about 3 mm particle size. The active ingredient is most conveniently applied to the clay by dissolving it in an inexpensive solvent, such as acetone, and applying the solution to the sized clay in an appropriate solids mixer. The solvent is then typically removed by evaporation prior to applying the granules to the application site.

When operating in accordance with the present invention, the present compounds, or compositions thereof, may be applied to the site where herbicidal control is desired by any convenient manner, e.g., by means of hand dusters or sprayers. Metering applicators can apply accurately measured quantities of granular compositions to the locus to be treated. Other applications can be carried out with power dusters, boom sprayers, high-pressure sprayers and spray dusters. In large scale operations, dusts or low-volume sprays can be applied aerially, for example from airplanes or helicopters, to the application site. When applying the formulations described above, it is important to apply the desired concentration of active ingredient uniformly to the plants or locus to be treated.

The herbicidal activity of representative compounds of the present invention is illustrated by the following experiments.

EXPERIMENT 1

The initial screen used to evaluate herbicidal efficacy was conducted at a test compound concentration of 15 lbs/acre (16.8 kg/ha). In this test a standard sand:soil mixture (1:1) was sterilized and added to separate containers and tomato, large crabgrass and pigweed seeds were planted by row. Each container was then fertilized before treatment.

The test compounds were formulated for application by dissolving the compound into a solvent prepared by combining Toximul R and Toximul S (proprietary blends of anionic and nonionic surfactants manufactured by Stepan Chemical Company, Northfield, Ill.) with a 1:1 (v/v) mixture of acetone:ethanol. The solvent/compound solution was diluted with deionized water and applied postemergence to some planted containers and preemergence to others using a DeVilbiss atomizer. Postemergence treatment was made 11 to 13 days after planting while preemergence treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows.

A=abscission of leaves
B=burned
C=chlorosis
D=death
E=epinasty
F=formative effects
G=dark green
I=increased plant growth
L=local necrosis
N=no germination
P=purple pigmentation
R=reduced germination
S=stunting
U=unclassified injury Table I presents the herbicidal activity of typical pyrazole derivatives of the invention when evaluated in the screen described above.

TABLE I

| | Herbicide Pretest at 15 lbs/acre (16.8 kg/ha) | | | | | |
|---|---|---|---|---|---|---|
| | Preemergence | | | Postemergence | | |
| Example No. of Compound Tested | Tomato | Large Crab-grass | Pig-weed | Tomato | Large Crab-grass | Pig-weed |
| 1 | 5N | 5N | 5N | 5D | 5D | 5D |
| 2 | 5N | 5N | 5N | 1 | 1 | 1 |
| 3 | 4RS | 5N | 5N | 5D | 5D | 5D |
| 4 | 1 | 1 | 1 | 1 | 1 | 2BS |
| 6 | 3BS | 4RS | 4RS | 5D | 3BS | 4BS |
| 7 | 1 | 2RS | 3RS | 1 | 1 | 1 |
| 8 | 1 | 3RS | 1 | 4BCS | 3S | 2CS |
| 9 | 1 | 2RS | 1 | 5D | 4BS | 5D |
| 11 | 1 | 1 | 1 | 1 | 1 | 1 |
| 12 | 5N | 5N | 5N | 5D | 5D | 5D |
| 13 | 1 | 1 | 2S | 2FS | 1 | 1 |
| 14 | 1 | 2S | 1 | 2BS | 1 | 1 |

EXPERIMENT 2

The herbicidal activity of some of the compounds of the present invention was further evaluated at various application rates in a multiple species greenhouse test. Several additional weed and crop species were utilized to determine the herbicidal activity and selectivity of the test compounds. Lower concentrations of the test compounds were obtained by serial dilution of the above described formulation with a mixture of the surfactant containing solvent and deionized water. The compounds were evaluated according to the general procedure outlined above. Table II presents the preemergence herbicidal test results, while Table III presents postemergence test data administered at 8 lbs/acre (8.96 kg/ha) or less. Both tables employ the following code for crop and weed species:

A=corn
B=cotton
C=soybean
D=wheat
E=alfalfa
F=sugar beets
G=rice
H=cucumber
I=tomato
J=barnyard grass
K=lambsquarter
L=large crabgrass
M=mustard
N=pigweed
O=foxtail
P=wild oats
Q=velvetleaf
R=jimsonweed
S=morning glory
T=zinnia

TABLE II

| Example No. of Compound Tested | Rate of Appln. (kg/ha) | Preemergence | | | | | | | | | | | | | | | | | | | |
|---|---|---|---|---|---|---|---|---|---|---|---|---|---|---|---|---|---|---|---|---|
| | | Crops | | | | | | | | Weeds | | | | | | | | | | | |
| | | A | B | C | D | E | F | G | H | I | J | K | L | M | N | O | P | Q | R | S | T |
| 1 | 8.0 (8.96) | | | | | | | | | 4 | 4 | | 5 | 3 | 5 | 5 | 4 | 5 | | 3 | 2 |

TABLE II-continued

Preemergence

| Example No. of Compound Tested | Rate of Appln. (kg/ha) | Crops | | | | | | | | | Weeds | | | | | | | | | | |
|---|---|---|---|---|---|---|---|---|---|---|---|---|---|---|---|---|---|---|---|---|---|
| | | A | B | C | D | E | F | G | H | I | J | K | L | M | N | O | P | Q | R | S | T |
| | 4.0 (4.48) | 2 | 1 | 1 | 2 | 2 | 2 | 2 | 3 | 4 | 5 | 5 | 5 | 4 | 5 | 5 | 2 | 3 | 4 | 1 | 2 |
| | 2.0 (2.24) | 2 | 1 | 1 | 1 | 1 | 1 | 1 | 1 | 2 | 3 | 5 | 4 | 3 | 5 | 5 | 2 | 3 | 3 | 1 | 2 |
| | 1.0 (1.12) | 1 | 1 | 1 | 1 | 1 | 1 | 1 | 1 | 1 | 3 | 4 | 1 | 2 | 2 | 3 | 1 | 1 | 1 | 2 | 2 |
| 2 | 8.0 (8.96) | | | | | | | | | 1 | 1 | | 2 | 2 | 4 | 4 | 1 | 4 | | 2 | 1 |
| | 4.0 (4.48) | 1 | 1 | 1 | 1 | 1 | 1 | 1 | 1 | 1 | 1 | 1 | 1 | 1 | 1 | 1 | 1 | 1 | 1 | 1 | 1 |
| | 2.0 (2.24) | 1 | 1 | 1 | 1 | 1 | 1 | 1 | 1 | 1 | 1 | 1 | 1 | 1 | 1 | 1 | 1 | 1 | 1 | 1 | 1 |
| | 1.0 (1.12) | 1 | 1 | 1 | 1 | 1 | 1 | 1 | 1 | 1 | 1 | 1 | 1 | 1 | 1 | 1 | 1 | 1 | 1 | 1 | 1 |
| 3 | 8.0 (8.96) | | | | | | | | | 4 | 4 | | 5 | 4 | 5 | 5 | 4 | 5 | | | 4 | 3 |
| | 4.0 (4.48) | 1 | 2 | 2 | 1 | 3 | 2 | 1 | 4 | 4 | 3 | 5 | 4 | 4 | 5 | 4 | 4 | 5 | 4 | 4 | 3 |
| | 2.0 (2.24) | 1 | 1 | 1 | 1 | 2 | 2 | 1 | 3 | 3 | 2 | 5 | 4 | 4 | 5 | 4 | 3 | 4 | 3 | 3 | 2 |
| | 1.0 (1.12) | 1 | 1 | 1 | 1 | 1 | 1 | 1 | 1 | 1 | 1 | 4 | 4 | 4 | 5 | 4 | 2 | 4 | 2 | 2 | 2 |
| | 1.0 (1.12) | 1 | 1 | 1 | 1 | 1 | 1 | 1 | 2 | 3 | 2 | 4 | 3 | 3 | 3 | 4 | 3 | 3 | 2 | 4 | 2 |
| | 0.5 (0.56) | 1 | 1 | 1 | 1 | 1 | 1 | 1 | 1 | 1 | 1 | 4 | 2 | 3 | 3 | 3 | 1 | 1 | 1 | 1 | 1 |
| | 0.25 (0.28) | 1 | 1 | 1 | 1 | 1 | 1 | 1 | 1 | 1 | 1 | 1 | 1 | 1 | 1 | 1 | 1 | 1 | 1 | 1 | 1 |
| 4 | 8.0 (8.96) | 1 | | | | | | | | | | 1 | | 1 | 1 | 1 | | 1 | | 1 | 1 |
| 5 | 8.0 (8.96) | | | | | | | | | 3 | 2 | | 4 | 2 | 4 | 5 | 2 | 4 | | | 1 | 2 |
| | 4.0 (4.48) | 1 | 1 | 2 | 1 | 1 | 1 | 2 | 3 | 3 | 1 | 5 | 3 | 1 | 5 | 4 | 2 | 3 | 2 | 2 | 1 |
| | 2.0 (2.24) | 1 | 1 | 1 | 1 | 1 | 1 | 1 | 1 | 1 | 1 | 5 | 2 | 1 | 2 | 4 | 1 | 1 | 3 | 1 | 1 |
| | 1.0 (1.12) | 1 | 1 | 1 | 1 | 1 | 3 | 1 | 2 | 1 | 1 | 4 | 1 | 4 | 2 | 2 | 1 | 5 | 4 | 1 | 2 |
| | 1.0 (1.12) | 1 | 1 | 1 | 1 | 2 | 1 | 1 | 1 | 1 | 1 | 1 | 1 | 1 | 1 | 1 | 1 | 1 | 1 | 1 | 1 |
| | 0.5 (0.56) | 1 | 1 | 1 | 1 | 1 | 1 | 1 | 1 | 1 | 1 | 3 | 1 | 1 | 1 | 1 | 1 | 1 | 1 | 1 | 1 |
| | 0.25 (0.28) | 1 | 1 | 1 | 1 | 1 | 1 | 1 | 1 | 1 | 1 | 4 | 1 | 3 | 2 | 1 | 1 | 1 | 2 | 1 | 2 |
| 6 | 8.0 (8.96) | | | | | | | | | 3 | 2 | | 4 | 3 | 5 | 4 | 4 | 5 | | | 3 | 2 |
| | 4.0 (4.48) | 3 | 1 | 2 | 1 | 2 | 2 | 1 | 4 | 3 | 2 | 5 | 3 | 4 | 4 | 2 | 4 | 4 | 3 | 3 |
| | 2.0 (2.24) | 2 | 1 | 1 | 1 | 1 | 1 | 1 | 1 | 1 | 1 | 3 | 1 | 1 | 3 | 3 | 1 | 1 | 3 | 1 | 2 |
| | 1.0 (1.12) | 1 | 1 | 1 | 1 | 1 | 1 | 1 | 1 | 1 | 1 | 1 | 1 | 1 | 2 | 1 | 1 | 1 | 2 | 1 | 2 |
| 7 | 8.0 (8.96) | | | | | | | | | 1 | 1 | | 4 | 1 | 5 | 4 | 1 | 2 | | 2 | 2 |
| | 4.0 (4.48) | 1 | 1 | 1 | 1 | 1 | 1 | 1 | 1 | 1 | 1 | 4 | 1 | 4 | 3 | 1 | 1 | 3 | 1 | 4 |
| | 2.0 (2.24) | 1 | 1 | 1 | 1 | 1 | 1 | 1 | 1 | 1 | 1 | 3 | 3 | 1 | 3 | 3 | 1 | 1 | 3 | 1 | 1 |
| | 1.0 (1.12) | 1 | 1 | 1 | 1 | 1 | 1 | 1 | 1 | 1 | 1 | 1 | 1 | 1 | 1 | 1 | 1 | 1 | 1 | 1 | 1 |
| 8 | 8.0 (8.96) | | | | | | | | | 1 | 1 | | 4 | 1 | 3 | 4 | 1 | 1 | | | 1 | 1 |
| | 4.0 (4.48) | 1 | 1 | 2 | 2 | 2 | 1 | 1 | 1 | 1 | 1 | 1 | 4 | 1 | 2 | 4 | 1 | 1 | 1 | 1 | 1 |
| | 2.0 (2.24) | 1 | 1 | 1 | 2 | 2 | 1 | 1 | 1 | 1 | 1 | 1 | 2 | 1 | 2 | 1 | 1 | 1 | 1 | 1 | 1 |
| | 1.0 (1.12) | 1 | 1 | 1 | 1 | 1 | 1 | 1 | 1 | 1 | 1 | 1 | 1 | 1 | 1 | 1 | 1 | 1 | 1 | 1 | 1 |
| 9 | 8.0 (8.96) | 1 | | | | | | | | | | 3 | | 1 | 2 | | 1 | | | 1 | 1 |
| 10 | 8.0 (8.96) | 3 | | | | | | | | | | 4 | | 5 | 5 | | 2 | | | 1 | 1 |
| | 4.0 (4.48) | 1 | 1 | 1 | 2 | 2 | 1 | 1 | 4 | 3 | 2 | 3 | 4 | 1 | 5 | 5 | 2 | 4 | 3 | 4 | 2 |
| | 2.0 (2.24) | 1 | 1 | 1 | 1 | 1 | 1 | 1 | 1 | 1 | 1 | 1 | 4 | 1 | 3 | 3 | 1 | 4 | 3 | 1 | 1 |
| | 1.0 (1.12) | 1 | 1 | 1 | 1 | 1 | 1 | 1 | 1 | 1 | 1 | 1 | 3 | 1 | 1 | 1 | 1 | 1 | 1 | 1 | 1 |
| 11 | 8.0 (8.96) | | | | | | | | | 2 | 1 | | 1 | 2 | 2 | 1 | 1 | | | 1 | 1 |
| 12 | 8.0 (8.96) | 3 | | | | | | | | | | 5 | | 5 | 5 | | 5 | | | 3 | 2 |
| | 4.0 (4.48) | 2 | 1 | 1 | 1 | 3 | 1 | 1 | 4 | 4 | 3 | 5 | 4 | 3 | 5 | 5 | 3 | 5 | 4 | 3 | 1 |
| | 2.0 (2.24) | 1 | 1 | 1 | 1 | 1 | 1 | 1 | 1 | 1 | 1 | | 4 | 1 | | 4 | 1 | 1 | 1 | 1 | 1 |
| | 1.0 (1.12) | 1 | 1 | 1 | 1 | 1 | 1 | 1 | 1 | 1 | 1 | | 3 | 1 | | 4 | 1 | 1 | 1 | 1 | 1 |
| 13 | 8.0 (8.96) | | | | | | | | | 1 | 1 | | 1 | 1 | 1 | 1 | 1 | 1 | | | 1 | 1 |
| 14 | 8.0 (8.96) | | | | | | | | | 2 | 1 | | 5 | 1 | 4 | 3 | 1 | 2 | | | 1 | 2 |
| | 4.0 (4.48) | 1 | 1 | 1 | 1 | 1 | 1 | 1 | 1 | 1 | 1 | 1 | 4 | 1 | 3 | 2 | 1 | 2 | 2 | 2 | 1 |
| | 2.0 (2.24) | 1 | 1 | 1 | 1 | 1 | 1 | 1 | 1 | 1 | 1 | 1 | 4 | 1 | 2 | 1 | 1 | 2 | 2 | 2 | 1 |
| | 1.0 (1.12) | 1 | 1 | 1 | 1 | 1 | 1 | 1 | 1 | 1 | 1 | 1 | 1 | 1 | 1 | 1 | 1 | 1 | 1 | 1 | 1 |
| 15 | 8.0 (8.96) | | | | | | | | | 2 | 1 | | 2 | 2 | 3 | 1 | 1 | 3 | | | 1 | 1 |
| 16 | 8.0 (8.96) | | | | | | | | | 1 | 1 | | 2 | 1 | 3 | 2 | 1 | 3 | | | 1 | 1 |

TABLE III

Postemergence

| Example No. of Compound Tested | Rate of Appln. lbs/acre (kg/ha) | A | I | L | N | O | Q | S | T | J | M | P |
|---|---|---|---|---|---|---|---|---|---|---|---|---|
| 1 | 8.0 (8.96) | 5 | 4 | 5 | 5 | 5 | 5 | 3 | 4 | 4 | 3 |
| | 4.0 (4.48) | 5 | 4 | 5 | 4 | 4 | 4 | 4 | 3 | 4 | 3 |
| | 2.0 (2.24) | 5 | 4 | 5 | 4 | 4 | 5 | 3 | 4 | 4 | 3 |
| | 1.0 (1.12) | 4 | 3 | 5 | 4 | 4 | 4 | 3 | 3 | 4 | 2 |
| | 1.0 (1.12) | 4 | 4 | 5 | 4 | 4 | 3 | 2 | 4 | 3 | 2 |
| | 0.5 (0.56) | 4 | 2 | 5 | 4 | 5 | 2 | 2 | 4 | 3 | 2 |
| | 0.25 (0.28) | 3 | 2 | 4 | 3 | 4 | 2 | 2 | 2 | 2 | 2 |
| | 0.25 (0.28) | 2 | 2 | 5 | 3 | 3 | 2 | 2 | 2 | 2 | 1 |
| | 0.125 (0.14) | 2 | 2 | 4 | 2 | 2 | 2 | 2 | 2 | 2 | 1 |
| | 0.0625 (0.07) | 1 | 1 | 3 | 2 | 1 | 2 | 2 | 1 | 1 | 1 |
| 2 | 8.0 (8.96) | 2 | 2 | 1 | 2 | 3 | 2 | 1 | 2 | 1 | 2 |
| 3 | 8.0 (8.96) | 5 | 4 | 5 | 4 | 5 | 4 | 4 | 3 | 4 | 2 |
| | 4.0 (4.48) | 5 | 3 | 5 | 4 | 5 | 5 | 4 | 3 | 4 | 2 |
| | 2.0 (2.24) | 4 | 3 | 5 | 4 | 5 | 5 | 3 | 2 | 4 | 2 |
| | 1.0 (1.12) | 4 | 3 | 5 | 4 | 5 | 5 | 2 | 2 | 3 | 2 |
| | 1.0 (1.12) | 3 | 1 | 5 | 2 | 4 | 2 | 3 | 2 | 3 | 2 |
| | 0.5 (0.56) | 3 | 1 | 4 | 2 | 4 | 2 | 2 | 2 | 3 | 1 |

TABLE III-continued

| Example No. of Compound Tested | Rate of Appln. lbs/acre (kg/ha) | Postemergence | | | | | | | | | | |
|---|---|---|---|---|---|---|---|---|---|---|---|---|
| | | A | I | L | N | O | Q | S | T | J | M | P |
| | 0.25 (0.28) | | 2 | 1 | 4 | 2 | 3 | 1 | 3 | 1 | 2 | 1 |
| 4 | 8.0 (8.96) | 1 | | 1 | 1 | 1 | 1 | 1 | 1 | | | |
| 5 | 8.0 (8.96) | | 4 | 2 | 4 | 4 | 4 | 3 | 2 | 2 | 3 | 2 |
| | 4.0 (4.48) | | 4 | 2 | 4 | 3 | 4 | 3 | 3 | 2 | 3 | 2 |
| | 2.0 (2.24) | | 4 | 2 | 5 | 4 | 5 | 4 | 3 | 2 | 4 | 2 |
| | 1.0 (1.12) | | 4 | 2 | 2 | 2 | 4 | 3 | 2 | 1 | 3 | 2 |
| | 1.0 (1.12) | | 3 | 1 | 1 | 2 | 3 | 1 | 2 | 1 | 1 | 1 |
| | 0.5 (0.56) | | 1 | 1 | 1 | 1 | 1 | 1 | 1 | 1 | 1 | 1 |
| | 0.25 (0.28) | | 1 | 1 | 1 | 1 | 1 | 1 | 1 | 1 | 1 | 1 |
| 6 | 8.0 (8.96) | | 4 | 3 | 4 | 3 | 5 | 4 | 3 | 2 | 3 | 4 |
| | 4.0 (4.48) | | | 2 | | 4 | 4 | 2 | 3 | 2 | 4 | |
| | 2.0 (2.24) | | 4 | 3 | | 4 | 4 | 2 | 3 | 2 | 4 | |
| | 1.0 (1.12) | | 3 | 1 | 4 | 2 | 4 | 2 | 2 | 1 | 2 | 4 |
| | 1.0 (1.12) | | 2 | 2 | 4 | 2 | 4 | 2 | 3 | 1 | 3 | 4 |
| | 0.5 (0.56) | | 2 | 1 | 2 | 2 | 3 | 2 | 2 | 2 | 2 | 2 |
| | 0.25 (0.28) | | 1 | 1 | 1 | 1 | 1 | 1 | 1 | 1 | 1 | 1 |
| 7 | 8.0 (8.96) | | 3 | 3 | 3 | 3 | 3 | 3 | 2 | 2 | 2 | 1 |
| 8 | 8.0 (8.96) | | 3 | 2 | 3 | 3 | 3 | 3 | 2 | 2 | 3 | 1 |
| 9 | 8.0 (8.96) | 1 | | 2 | 1 | 2 | 2 | 1 | 2 | | | |
| 10 | 8.0 (8.96) | 3 | | 4 | 5 | 4 | 5 | 4 | 3 | | | |
| | 4.0 (4.48) | 3 | | 2 | 3 | 4 | 4 | 4 | 3 | | | |
| | 2.0 (2.24) | 2 | | 2 | 2 | 4 | 4 | 3 | 3 | | | |
| | 1.0 (1.12) | 2 | | 3 | 2 | 3 | 3 | 3 | 3 | | | |
| 11 | 8.0 (8.96) | | 1 | 2 | 2 | 2 | 2 | 1 | 1 | 1 | 2 | 1 |
| 12 | 8.0 (8.96) | 3 | | 4 | 5 | 4 | 5 | 4 | 2 | | | |
| | 4.0 (4.48) | 2 | | 3 | 4 | 4 | 5 | 4 | 2 | | | |
| | 2.0 (2.24) | 2 | | 3 | 4 | 4 | 5 | 4 | 2 | | | |
| | 1.0 (1.12) | 1 | | 2 | 3 | 3 | 5 | 3 | 2 | | | |
| | 1.0 (1.12) | 2 | | 1 | 3 | 2 | 3 | 2 | 1 | | | |
| | 0.5 (0.56) | 2 | | 1 | 1 | 2 | 3 | 2 | 1 | | | |
| | 0.25 (0.28) | 2 | | 1 | 1 | 1 | 2 | 1 | 1 | | | |
| 13 | 8.0 (8.96) | | 2 | 3 | 2 | 2 | 3 | 1 | 2 | 2 | 2 | 1 |
| 14 | 8.0 (8.96) | | 2 | 2 | 1 | 2 | 2 | 2 | 1 | 1 | 2 | 1 |
| 15 | 8.0 (8.96) | | 4 | 2 | 4 | 4 | 4 | 3 | 3 | 3 | 5 | 2 |
| 16 | 8.0 (8.96) | | 1 | 1 | 1 | 2 | 2 | 2 | 1 | 1 | 1 | 1 |

We claim:
1. A compound of the formula

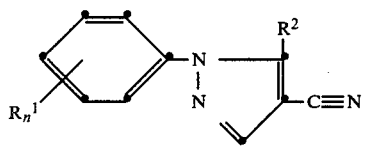

wherein each $R^1$ independently is halogen; $R^2$ is halo or trifluoromethyl; and n is 1–5;
with the provisos that when n is 1, $R^1$ is other than fluorine, and when n is 2 and each $R^1$ is chlorine, at least one $R^1$ is located at a para or ortho position on the phenyl ring.

2. The compound of claim 1 which is 5-chloro-1-(2,3,4-trichlorophenyl)-1H-pyrazole-4-carbonitrile.

3. The compound of claim 1 which is 5-chloro-1-(2,4-difluorophenyl)-1H-pyrazole-4-carbonitrile.

4. The compound of claim 1 which is 5-chloro-1-(2,4,6-trichlorophenyl)-1H-pyrazole-4-carbonitrile.

5. The compound of claim 1 which is 5-chloro-1-(2,4-dibromophenyl)-1H-pyrazole-4-carbonitrile.

6. The compound of claim 1 which is 5-chloro-1-(2,3-dichlorophenyl)-1H-pyrazole-4-carbonitrile.

7. The compound of claim 1 which is 5-chloro-1-(2,4,5-trichlorophenyl)-1H-pyrazole-4-carbonitrile.

8. The compound of claim 1 which is 5-chloro-1-(2,4-dichlorophenyl)-1H-pyrazole-4-carbonitrile.

9. The compound of claim 1 which is 5-(trifluoromethyl)-1-(2,4-dichlorophenyl)-1H-pyrazole-4-carbonitrile.

10. A composition which comprises a plant-growth inhibiting amount of a compound of claim 1 and an agriculturally-acceptable carrier.

11. The composition of claim 10 wherein the compound is 5-chloro-1-(2,3,4-trichlorophenyl)-1H-pyrazole-4-carbonitrile.

12. The composition of claim 10 wherein the compound is 5-chloro-1-(2,4-difluorophenyl)-1H-pyrazole-4-carbonitrile.

13. The composition of claim 10 wherein the compound is 5-chloro-1-(2,4,6-trichlorophenyl)-1H-pyrazole-4-carbonitrile.

14. The composition of claim 10 wherein the compound is 5-chloro-1-(2,4-dibromophenyl)-1H-pyrazole-4-carbonitrile.

15. The composition of claim 10 wherein the compound is 5-chloro-1-(2,3-dichlorophenyl)-1H-pyrazole-4-carbonitrile.

16. The composition of claim 10 wherein the compound is 5-chloro-1-(2,4,5-trichlorophenyl)-1H-pyrazole-4-carbonitrile.

17. The composition of claim 10 wherein the compound is 5-chloro-1-(2,4-dichlorophenyl)-1H-pyrazole-4-carbonitrile.

18. The composition of claim 10 wherein the compound is 5-(trifluoromethyl)-1-(2,4-dichlorophenyl)-1H-pyrazole-4-carbonitrile.

19. A method for controlling undesired plants which comprises applying to the plants a growth inhibiting amount of a compound of claim 1.

20. The method of claim 19 wherein the compound is 5-chloro-1-(2,3,4-trichlorophenyl)-1H-pyrazole-4-carbonitrile.

21. The method of claim 19 wherein the compound is 5-chloro-1-(2,4-difluorophenyl)-1H-pyrazole-4-carbonitrile.

22. The method of claim 19 wherein the compound is 5-chloro-1-(2,4,6-trichlorophenyl)-1H-pyrazole-4-carbonitrile.

23. The method of claim 19 wherein the compound is 5-chloro-1-(2,4-dibromophenyl)-1H-pyrazole-4-carbonitrile.

24. The method of claim 19 wherein the compound is 5-chloro-1-(2,3-dichlorophenyl)-1H-pyrazole-4-carbonitrile.

25. The method of claim 19 wherein the compound is 5-chloro-1-(2,4,5-trichlorophenyl)-1H-pyrazole-4-carbonitrile.

26. The method of claim 19 wherein the compound is 5-chloro-1-(2,4-dichlorophenyl)-1H-pyrazole-4-carbonitrile.

27. The method of claim 19 wherein the compound is 5-(trifluoromethyl)-1-(2,4-dichlorophenyl)-1H-pyrazole-4-carbonitrile.

* * * * *